United States Patent
Krug et al.

(10) Patent No.: US 10,863,905 B2
(45) Date of Patent: Dec. 15, 2020

(54) OCT SYSTEM

(71) Applicant: OptoMedical Technologies GmbH, Lübeck (DE)

(72) Inventors: Marc Krug, Lübeck (DE); Eva Lankenau, Lübeck (DE)

(73) Assignee: OptoMedical Technologies GmbH, Lubeck (DE)

( * ) Notice: Subject to any disclaimer, the term of this patent is extended or adjusted under 35 U.S.C. 154(b) by 132 days.

(21) Appl. No.: 16/089,047

(22) PCT Filed: Mar. 30, 2017

(86) PCT No.: PCT/EP2017/057491
§ 371 (c)(1),
(2) Date: Sep. 27, 2018

(87) PCT Pub. No.: WO2017/167850
PCT Pub. Date: Oct. 5, 2017

(65) Prior Publication Data
US 2020/0129067 A1 Apr. 30, 2020

(30) Foreign Application Priority Data
Mar. 31, 2016 (DE) .......... 10 2016 205 370

(51) Int. Cl.
*G01B 9/02* (2006.01)
*A61B 5/00* (2006.01)

(52) U.S. Cl.
CPC ........ *A61B 5/0066* (2013.01); *G01B 9/02019* (2013.01); *G01B 9/02021* (2013.01); *G01B 9/02091* (2013.01)

(58) Field of Classification Search
CPC ............ G01B 9/02091; G01B 9/02015; G01B 9/02027; G01B 9/02028; G01B 9/02049
See application file for complete search history.

(56) References Cited

U.S. PATENT DOCUMENTS

| 6,501,551 B1 | 12/2002 | Tearney et al. |
| 2007/0278389 A1* | 12/2007 | Ajgaonkar ......... G01B 9/02028 250/221 |

(Continued)

FOREIGN PATENT DOCUMENTS

| EP | 0327566 B1 | 4/1993 |
| EP | 1983920 B1 | 8/2016 |

OTHER PUBLICATIONS

International Search Report dated Jun. 21, 2017 (PCT/EP2017/057491).

*Primary Examiner* — Jonathan M Hansen
(74) *Attorney, Agent, or Firm* — Alix, Yale & Ristas, LLP

(57) ABSTRACT

The invention relates to an OCT system comprising an OCT light source, an OCT evaluation unit, a first OCT light guide, a second OCT light guide and a changeover module. The light from the OCT light source passes through the changeover module. In a first state of the changeover module, the OCT light is passed to an entry end of the first OCT light guide. In a second state of the changeover module, the OCT light is passed to an entry end of the second OCT light guide. A scanning device assigned to the first OCT light guide is arranged between the changeover module and the object plane. The OCT system according to the invention can be used in a flexible manner.

12 Claims, 3 Drawing Sheets

(56) References Cited

U.S. PATENT DOCUMENTS

| | | | |
|---|---|---|---|
| 2010/0041986 A1 | 2/2010 | Nguyen et al. | |
| 2011/0299034 A1* | 12/2011 | Walsh | A61B 3/0091 351/206 |
| 2015/0201833 A1 | 7/2015 | Chong | |

* cited by examiner

OCT SYSTEM

BACKGROUND

The invention relates to an OCT system comprising an OCT light source and an OCT evaluation unit. The invention also relates to an associated method.

Optical coherence tomography (OCT) is an imaging method known in the prior art. Short-coherent OCT light is passed to an object, in particular human tissue, and scattering centers in the object are inferred from the reflected portions of the light. The light reflected by the object and the light of a reference beam path are superimposed in the OCT evaluation unit. The image information is obtained by evaluating the interference pattern of the two beam paths.

The light coming from the OCT light source is passed to the object via a light guide. The light emerging from the exit end of the light guide strikes the object. The reflected portions of the light enter the light guide again and are guided back to the OCT evaluation unit via the light guide. The arrangement and orientation of the light guide therefore decisively determine which OCT information can be obtained. Some retrofitting effort is needed to obtain a different item of OCT information using the same OCT device.

SUMMARY OF THE INVENTION

The invention is based on the object of presenting an OCT system and an associated method which provides more flexible possible uses. On the basis of the cited prior art, the object is achieved with the features of the independent claims. Advantageous embodiments are specified in the subclaims.

According to the invention, the OCT system comprises a first OCT light guide, a second OCT light guide and a changeover module. The light from the OCT light source passes through the changeover module. The OCT light is passed to an entry end of the first light guide in a first state of the changeover module. The OCT light is passed to an entry end of the second OCT light guide in a second state of the changeover module. A scanning device assigned to the first OCT light guide is arranged between the changeover module and the object plane.

The changeover module according to the invention makes it possible to obtain different items of OCT information in a fast and uncomplicated manner using the OCT system. If the OCT light is passed into the object plane via the first light guide and the scanning device, an item of areal image information can be obtained. If the OCT light passes through the second light guide, the OCT light reaches the associated object plane in a manner uninfluenced by the scanning device assigned to the first light guide. A different item of OCT information can therefore be obtained via the second OCT light guide than via the first OCT light guide. This opens up a plurality of novel possible applications.

The OCT system preferably comprises an intermediate light guide which is arranged between the OCT light source and the changeover module. The intermediate light guide is connected to an input side of the changeover module. The terms input and output are used with respect to the direction of movement from the OCT light source to the object area. The optical elements of the OCT system can be crossed in the reverse direction on the return path of the OCT light.

The changeover module can have a first output and a second output, wherein the first OCT light guide is connected to the first output, and wherein the second OCT light guide is connected to the second output. A flexible light guide section is preferably provided inside the changeover module, one end of which section is connected to the input side of the changeover module. The other end of the flexible light guide section can preferably be coupled either to the first output or to the second output of the changeover module. The OCT light is therefore passed either into the first OCT light guide or into the second OCT light guide. It is also possible for the changeover module to have a plurality of light guide ends which are arranged in a fixed position and for the changeover module to comprise a movable optical element which is used to introduce the OCT light into different light guides.

A mechanical changeover switch can be provided in the changeover module and is designed to move the one end of the flexible light guide section. The other end of the light guide preferably remains in an unchanged position during changeover. The changeover switch may be, for example, a rotating mechanism or a sliding mechanism.

The changeover between the first OCT light guide and the second OCT light guide is preferably triggered by a control signal, in particular an electrical control signal. The control signal can be triggered by an operation carried out by an operator, for example by virtue of the operator actuating a switch or making an input.

Additionally or alternatively, the control signal can also be generated by a control unit. The control unit may be designed, for example, to generate the control signal automatically according to a predefined temporal sequence. This opens up the possibility, inter alia, of carrying out different measurements in a virtually parallel manner by changing over between the two OCT light guides within very short intervals of time. This is of interest, for example, when the properties of the object being examined change over the course of time.

In order to obtain an item of meaningful information using the OCT system, the OCT beam path should be focused in the object plane.

Consequently, an item of substantially punctiform image information can be obtained by means of an OCT beam which is aimed at a particular position in the object plane using the second OCT light guide. This is sufficient for particular applications, for example if the OCT system is intended to be used to determine the distance between an exit end of the OCT light guide and an object.

For an item of two-dimensional image information, the object must be scanned using the OCT beam. The OCT been is therefore moved in the object plane in order to compose a two-dimensional image from a multiplicity of items of punctiform image information. For this purpose, the first OCT light guide is assigned a scanning device which is designed to deflect the OCT beam in such a manner that the OCT beam scans an object plane. If a scanning device is assigned to one of the OCT light guides, an OCT beam passing through the other OCT light guide cannot be influenced by this scanning device.

The scanning device can be designed, for example, in such a manner that the exit end of the OCT light guide is moved in order to deflect the OCT beam in the desired manner. In one preferred embodiment, a scanning device is arranged between the exit end of the OCT light guide and the object plane and deflects the OCT beam in the desired manner. The scanning device may comprise one or more movable mirrors which deflect the OCT beam. In one variant, the scanning device comprises two scanning mirrors which are mounted such that they can be pivoted about axes which are orthogonal to one another.

The OCT system may comprise a control unit which controls the scanning device. The relevant control signals can be electrically transmitted from the control unit to the scanning device. In one preferred embodiment, the transmission path for the control signals extends through the control module.

The OCT system according to the invention can be set up in such a manner that a scanning device is provided only for the first OCT light guide. Such an OCT system can be used, for example, if a two-dimensional image is intended to be obtained using the first OCT light guide, whereas the other light guide is intended to be used to measure the distance between an exit end of the light guide and an object.

In other cases, it may be desirable to obtain an item of two-dimensional image information using both OCT light guides. The OCT system can therefore comprise a first scanning device assigned to the first OCT light guide and a second scanning device assigned to the second OCT light guide. Both scanning devices can be controlled by a control unit of the OCT system, in which case the transmission paths for both scanning devices can extend through the changeover module. In one preferred embodiment, the control of the scanning devices is coupled to the control of the changeover module. This means that the control signals from the control unit are always aimed at the scanning device of that OCT light guide through which the OCT light is also currently being passed. This enables various automated sequences in which the system switches back and forth between the two OCT light guides.

For example, an electrical changeover switch can be provided in the changeover module and can be used to change between the two scanning devices. The electrical changeover switch can be controlled using the same control signal which is also used to change over between the two OCT light guides. A scanning device is therefore activated with the changeover between the first OCT light guide and the second OCT light guide.

In order to compensate for different optical paths between the two OCT light guides, a compensation unit for adjusting the optical paths can be assigned to one or both of the OCT light guides. If the optical paths have different lengths, the compensation unit preferably comprises an additional air gap through which the OCT light is passed. If a dispersion difference is associated with the two optical paths, the compensation unit preferably comprises an optical element for compensating for the dispersion. If the two optical paths result in a polarization difference, the compensation unit preferably comprises an optical element for compensating for the polarization, in particular a polarization controller. The compensation unit can be designed to compensate for one or more of these differences.

In one embodiment, the system according to the invention comprises a surgical microscope, wherein the beam path of the first OCT light guide is guided through the main objective of the surgical microscope. The OCT beam path can be coupled into the observation beam path of the surgical microscope via the camera port or via the illumination beam path, for example. The scanning device assigned to the first light guide is preferably arranged between the changeover module and the main objective of the surgical microscope.

The second OCT light guide may be connected to a surgical instrument, as a result of which it becomes possible to determine the distance between an instrument head and an object. This can be used during surgical operations to prevent injuries from being inadvertently inflicted with the surgical instrument. The OCT beam can be aimed at the region in front of the instrument head. It is also possible for the OCT beam to additionally cover part of the instrument head, with the result that the distance can be directly determined by means of an OCT evaluation.

In an alternative embodiment, the second OCT light guide is also provided with a scanning device. The second OCT light guide can be connected, for example, to an OCT handpiece which is placed directly onto the tissue to be examined. Alternatively, the second OCT light guide can be coupled into the beam path of an endoscope. The possibility of being able to record OCT images from different perspectives using the surgical microscope and the OCT handpiece or endoscope is provided. Other combinations of the optical devices mentioned and other instruments are also included in the invention.

A changeover module which can change over between more than two states is also possible, wherein a different OCT light guide is active in each of the states. For example, the changeover module can be designed to change over between three or four OCT light guides.

The changeover module can be configured as a separate structural unit which is arranged between an OCT unit and the OCT light guides. It is also possible to integrate the changeover module in a housing of the OCT unit. The housing of the OCT unit then preferably has a plurality of outputs to which OCT light guides can be connected.

The invention also relates to a method for carrying out an OCT measurement. In the method, OCT light from an OCT light source is passed to an object via a changeover module and a first OCT light guide and a scanning device, and the light reflected by the object is evaluated in an OCT evaluation unit. The changeover module is actuated in order to pass the OCT light from the OCT light source to an object via a second OCT light guide, and the light reflected by the object is evaluated in the OCT evaluation unit. The method can be developed with further features which are described within the scope of the system according to the invention. The system can be developed with further features which are described in the context of the method according to the invention.

BRIEF DESCRIPTION OF THE DRAWINGS

The invention is described by way of example below on the basis of advantageous embodiments with reference to the accompanying drawings, in which.

DETAILED DESCRIPTION

Figure 1:
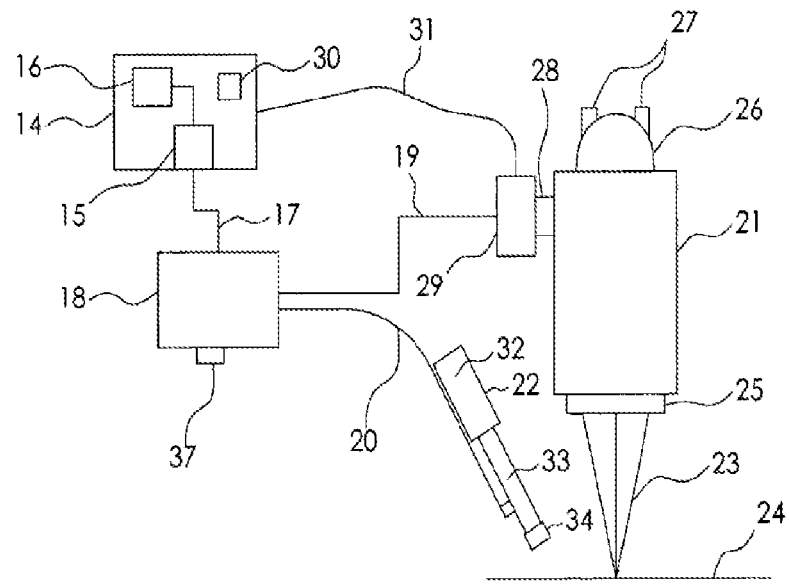
FIG. 1 shows a schematic illustration of an OCT system according to the invention.

According to FIG. 1, an OCT system according to the invention comprises an OCT device 14 in which an OCT light source 15 and an OCT evaluation unit 16 are arranged. Light emitted by the OCT light source is passed to the input side of a changeover module 18 via an intermediate light guide 17.

A first OCT light guide 19 and a second OCT light guide 20 are connected to an output side of the changeover module 18. The first OCT light guide 19 extends to a surgical microscope 21. The second OCT light guide 20 extends to a surgical instrument 22.

The surgical microscope defines a stereoscopic observation beam path 23 which extends from an object plane 24, through a main objective 25, a magnification system with variable magnification which is not visible in FIG. 1, to a viewer 26 having two eyepieces 27. An observer sees a magnified image from the object plane 24 in the eyepieces 27.

The first OCT light guide 19 extends to a camera port 28 of the surgical microscope 21. A beam splitter is arranged in the observation beam path of the surgical microscope 21 and couples out part of the light coming from the object plane and deflects it in the direction of the camera port 28. Conversely, light supplied via the camera port 28 is coupled into the observation beam path and moves into the object plane 24 along the observation beam path.

Optical elements are arranged in the OCT beam path, which extends from the OCT device 14 into the object plane 24 via the changeover module 18, the first OCT light guide 19 and the surgical microscope 21, in such a manner that the OCT beam path is focused in an OCT object plane. The OCT object plane can coincide with the object plane 24 of the surgical microscope. The OCT object plane may also lie slightly below the surface of the object since it is possible to penetrate human tissue to a certain extent with the OCT light.

An item of punctiform image information can be obtained in this manner from the OCT object plane using the OCT beam path. In order to obtain an item of two-dimensional image information from which supplementary information relating to the optical image visible in the surgical microscope 21 arises, the object is scanned using the OCT beam. For this purpose, a scanning device 29 is arranged between the first OCT light guide 19 and the camera port 28. The scanning device 29 comprises two scanning mirrors which are mounted in such a manner that they can be pivoted about axes orthogonal to one another and are equipped with drives for a relevant pivoting movement. Embodiments in which the scanning is carried out by means of a single scanning mirror which is deflected in two directions using a MEMS (micro-electronic mechanical system) are also possible. The drives are controlled by a controller 30 of the OCT device in a suitable manner via an electrical cable 31, with the result that the OCT beam scans the object plane. The OCT evaluation unit 16 can compose a two-dimensional image from the sum of items of punctiform image information.

The surgical instrument 22 extends from a handle 32, via a shaft 33, to an instrument head 34. The exit end of the second OCT light guide 20 is connected to the shaft 33 of the surgical instrument 22. The exit end of the second OCT light guide 20 is oriented in such a manner that the OCT beam extends substantially parallel to the longitudinal direction of the surgical instrument 22. The OCT beam can extend past the instrument head or can partially capture the instrument head. In both cases, an item of punctiform image information can be obtained from the region in front of the instrument head 34 using the OCT beam.

The punctiform image information is evaluated in the evaluation unit 16 of the OCT device 14 in order to determine the distance between the instrument head 34 of the surgical instrument 22 and an object arranged in front of the instrument head 34. In this manner, a surgeon can carry out ongoing distance control and can therefore ensure that he does not inadvertently come into contact with the tissue and therefore inflict an injury. If the OCT beam additionally partially captures the instrument head, the distance between the instrument head and the object can be directly measured.

The OCT device 14 can evaluate the signals from the first OCT light guide 19 and from the second OCT light guide only in temporal succession, rather than at the same time. The changeover module 18 is designed to couple the intermediate light guide 17 either to the first OCT light guide 19 or to the second OCT light guide 20. This ensures that only one of the OCT light guides 19, 20 is active at any time.

Figure 2:
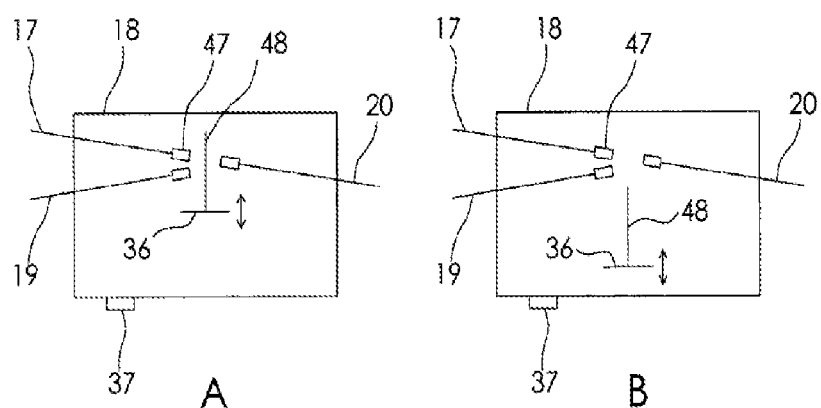
FIG. 2 shows a schematic illustration of a changeover module according to the invention in two states A, B.

According to FIG. 2, the changeover module 18 comprises an input, to which the intermediate light guide 17 is connected, and two outputs, to which the first OCT light guide 19 and the second OCT light guide 20 are connected. All light guides 17 lead to a respective collimator 47 inside the changeover module 18. The changeover module 18 comprises a changeover switch 36 which can be used to move a mirror 48 arranged between the collimators 47. In a first position (FIG. 2A) of the changeover switch 36, the mirror 48 is arranged in front of the collimator 47 of the intermediate light guide 17, with the result that light emerging from the intermediate light guide 17 is reflected to the first OCT light guide 19. In a second position (FIG. 2B), the mirror 48 has been moved downward, with the result that the light emerging from the intermediate light guide 17 passes directly into the second OCT light guide 20.

The changeover module 18 comprises an actuation button 37 in order to change over between the two states of the changeover switch 36. The actuation button 37 is actuated by the surgeon if necessary. If the surgeon would like an item of supplementary OCT image information relating to the optical image in the surgical microscope 21, he changes the changeover module 18 to the first switching state. If the surgeon would like an item of information relating to the distance between the instrument head 34 of the surgical instrument 22 and an object arranged in front of the head, he changes the changeover module 18 to the second switching state.

With the changeover of the changeover module 18, a control signal is simultaneously transmitted to the OCT device 14, with the result that the OCT device 14 receives the information relating to which of the two OCT light guides 19, 20 is active. If the first OCT light guide 19 is active, the controller 30 transmits control signals to the scanning device 29 and the OCT evaluation unit 16 evaluates the OCT image information from the object plane. If the second OCT light guide 20 is active, the controller 30 remains inactive and the evaluation unit 16 determines the distance between the instrument head 34 and an object.

Figure 3:
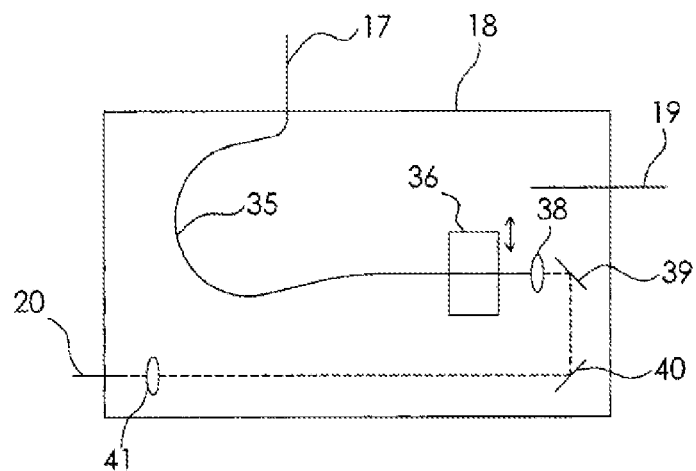
FIG. 3 shows an alternative embodiment of a changeover module according to the invention.

For the evaluation of the OCT signal, it is advantageous if the optical path via the first OCT light guide 19 is exactly the same length as the optical path via the second OCT light guide 20. This is not readily the case since a longer air path needs to be covered between the main objective 25 of the surgical microscope 21 and the object plane 24, whereas the instrument head 34 of the surgical instrument 22 is brought close to the object plane. In order to compensate for this, the OCT system according to the invention may comprise a compensation path. In the exemplary embodiment in FIG. 3, the compensation path is arranged in a changeover module 18 in which a flexible light guide section 35 is coupled either to the first OCT light guide 19 or to the second OCT light guide 20 via a changeover switch 36. In a switching position of the changeover switch 36, a first lens 38 which converts the OCT light into a collimated beam is arranged in front of the exit end of the flexible light guide section 35, with the result that the OCT beam can overcome an air gap which extends via two mirrors 39, 40 and a second lens 41, via which the OCT light is supplied to the entry end of the second OCT light guide 20.

Figure 4:
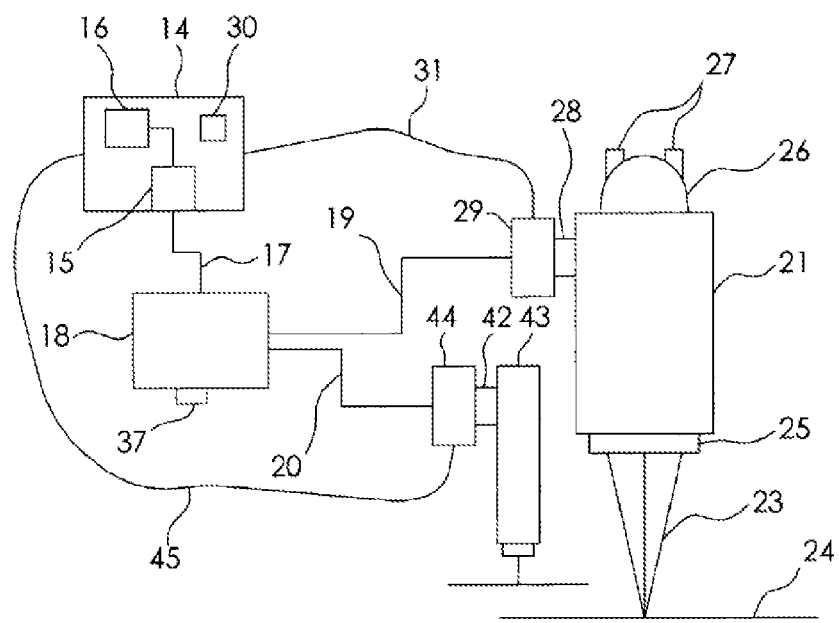
FIG. 4 shows an alternative embodiment of an OCT system according to the invention.

In the second exemplary embodiment of a system according to the invention, as illustrated in FIG. 4, the second OCT light guide 20 extends to a camera port 42 of an endoscope 43. A second scanning device 44 is arranged between the exit end of the second OCT light guide 20 and the camera port 42 and is likewise controlled by the controller 30 of the OCT device 14 via a second electrical line 45.

The surgeon can change over between the surgical microscope 21 and the endoscope 43 by actuating the changeover switch 18. In the first switching position of the changeover switch 18, the surgeon receives an item of supplementary OCT image information relating to the optical image in the surgical microscope 21. In the second switching position of the changeover switch 18, the surgeon receives an item of supplementary image information relating to the optical image in the endoscope 43.

Figure 5:
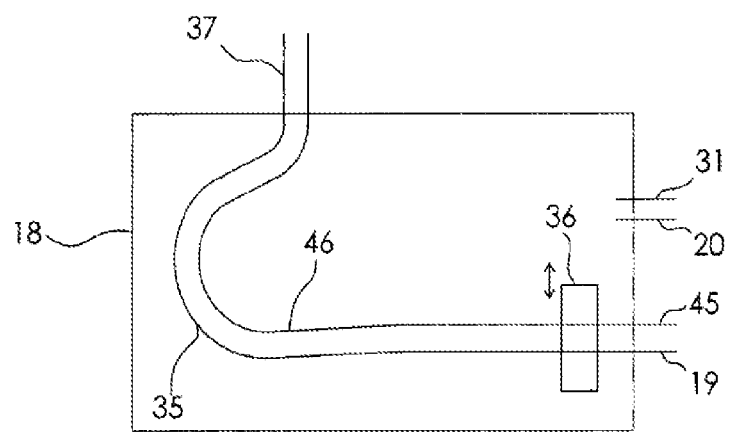
FIG. 5 shows the view according to FIG. 3 in another embodiment of a changeover module according to the invention.

FIG. 5 illustrates an embodiment of a changeover module 18 according to the invention in which the changeover module 18 comprises a flexible light guide section 35, the input side of which is connected to the intermediate light guide 17. The changeover switch 36 can be used to couple the flexible light guide section 35 either to the first OCT light guide 19 or to the second OCT light guide 20. The changeover switch 36 does not only change over between the two OCT light guides 19, 20 but also between the two electrical lines 31, 45. In addition to the flexible light guide section 35, an electrical cable 46 coming from the OCT device 14 therefore extends through the changeover switch 18.

Figure 6:
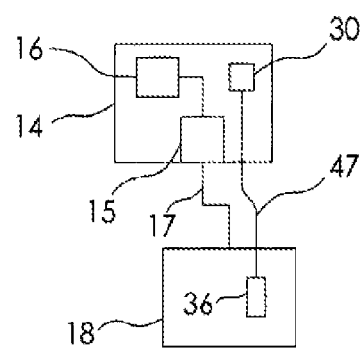
FIG. 6 shows an OCT device and a changeover module in another embodiment of a system according to the invention.

FIG. 6 shows an embodiment in which the changeover switch 36 is controlled by the controller 30 of the OCT device 14 by means of a control signal. The changeover between the first OCT light guide 19 and the second OCT light guide 20 is therefore carried out without manual intervention.

The invention claimed is:

1. An OCT system comprising:
    a surgical microscope (21) having an observation beam path (23) and an object plane (24);
    an OCT light source (15) generating OCT light;
    a changeover module (18) operatively coupled to receive said OCT light from said OCT light source;
    a first OCT light guide (19) having an entry end operatively coupled to said changeover module and defining a first OCT beam path coupled into said observation beam path (23);
    a scanning device (29) assigned to the first OCT light guide (19);
    a second OCT light guide (20) having an entry end operatively coupled to said changeover module and defining a second OCT beam path coupled into a beam path of an optical device, a surgical instrument (22), or an OCT handpiece; and
    an OCT evaluation unit,
    wherein OCT light from the OCT light source (15) passes through the changeover module (18), said OCT light is passed to the entry end of the first OCT light guide (19) in a first state of the changeover module (18), said OCT light is passed to the entry end of the second OCT light guide (20) in a second state of the changeover module (18), and wherein said scanning device (29) is arranged between the changeover module (18) and said object plane.

2. The OCT system of claim 1, wherein the changeover module (18) comprises a mechanical changeover switch (36) and a flexible light guide section (35), and the changeover switch (36) is designed to move one end of the flexible light guide section (35).

3. The OCT system of claim 1, wherein a changeover between the first state of said changeover module (18) and the second state of said changeover module (18) is triggered by a control signal.

4. The OCT system of claim 3, wherein the control signal is generated by a control unit (30) of the OCT system.

5. The OCT system of claim 1, comprising a scanning device (44) assigned to the second OCT light guide (20) is arranged between the changeover module (18) and the object plane.

6. The OCT system of claim 5, wherein a scanning device (29, 44) is activated with the changeover between the first OCT light guide (19) and the second OCT light guide (20).

7. The OCT system of claim 1, comprising a compensation unit (38, 39, 40, 41) for compensating for path length differences, polarization differences and/or dispersion differences is assigned to the first OCT light guide (19) and/or the second OCT light guide (20).

8. The OCT system of claim 1, wherein the system is designed to carry out a distance measurement between an exit end of the OCT light guide (19, 20) and an object using the first OCT light guide (19) and/or the second OCT light guide (20).

9. The OCT system of claim 1, wherein the changeover module (18) is designed to change over between more than two OCT light guides.

10. A method for carrying out an OCT measurement comprising the steps of:
    generating OCT light from an OCT light source (15);
    passing said OCT light to an object via a changeover module (18), a first OCT light guide (19), a scanning device (29), and an observation beam path (23) of a surgical microscope (21); and
    evaluating the light reflected by the object in an OCT evaluation unit (16); or
    actuating the changeover module (18) to pass said OCT light from the OCT light source (15) to an object via a second OCT light guide (20) and a beam path of an optical device, a surgical instrument (22), or an OCT handpiece; and
    evaluating the light reflected by the object in the OCT evaluation unit (16).

11. The method of claim 10, wherein said step of actuating comprises passing said OCT light from the OCT light source (15) to a beam path of an optical device, wherein said optical device is a second surgical microscope (21) or an endoscope (43).

12. The OCT system of claim 1, wherein said optical device is a second surgical microscope (21) or an endoscope (43).

* * * * *